(12) United States Patent
Haveri

(10) Patent No.: US 10,342,456 B2
(45) Date of Patent: Jul. 9, 2019

(54) APPARATUS, ARRANGEMENT AND METHOD FOR ANALYZING BREATHING GAS FLOWING ALONG BREATHING TUBING FOR SUBJECT BREATHING

(71) Applicant: General Electric Company, Schenectady, NY (US)

(72) Inventor: Heikki Antti Mikael Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 593 days.

(21) Appl. No.: 13/768,183

(22) Filed: Feb. 15, 2013

(65) Prior Publication Data

US 2013/0218040 A1 Aug. 22, 2013

(30) Foreign Application Priority Data

Feb. 17, 2012 (EP) .................................... 12155867

(51) Int. Cl.
*A61M 16/08* (2006.01)
*A61B 5/08* (2006.01)
(Continued)

(52) U.S. Cl.
CPC .............. *A61B 5/082* (2013.01); *A61B 5/097* (2013.01); *A61M 16/085* (2014.02);
(Continued)

(58) Field of Classification Search
CPC ....... A61B 5/4839; A61B 5/097; A61B 5/082; A61M 11/00; A61M 16/085;
(Continued)

(56) References Cited

U.S. PATENT DOCUMENTS 4,907,166 A * 3/1990 Corenman ............. A61B 5/083
600/532
5,322,057 A 6/1994 Raabe et al.
(Continued)

FOREIGN PATENT DOCUMENTS

| CN | 1654095 A | 8/2005 |
| CN | 1676173 A | 10/2005 |
| CN | 1772315 A | 5/2006 |

OTHER PUBLICATIONS

European Search Report and Written Opinion from corresponding European Application No. 12155867.0, dated Jul. 25, 2012.
(Continued)

*Primary Examiner* — Peter S Vasat

(57) ABSTRACT

An apparatus and method is provided for analyzing a breathing gas flowing along a breathing tubing for subject breathing. The breathing gas comprises breathing cycles having different phases. Liquid particles can be delivered intermittently depending on the phase, or continuously into the breathing gas. The apparatus comprises a gas sample supplier for adjusting gas sample supply from the breathing gas, and a gas analyzer for receiving the gas sample adjusted by the gas sample supplier and for measuring the gas sample property. The apparatus further comprises a processing unit for receiving a signal indicative of one of the phases of the breathing cycle and the delivery timing of the liquid particles. The processing unit is able to control the sample supplier based on the signal to limit access of liquid particles with the gas sample towards the gas analyzer.

14 Claims, 2 Drawing Sheets

(51) Int. Cl.
  *A61B 5/097* (2006.01)
  *A61M 16/14* (2006.01)
  *A61M 11/00* (2006.01)
  *A61B 5/00* (2006.01)
  *A61M 16/16* (2006.01)
  *A61M 16/00* (2006.01)
  *A61M 16/10* (2006.01)

(52) U.S. Cl.
  CPC ........... *A61M 16/14* (2013.01); *A61B 5/4839* (2013.01); *A61M 11/00* (2013.01); *A61M 16/1065* (2014.02); *A61M 16/16* (2013.01); *A61M 2016/0021* (2013.01); *A61M 2016/0027* (2013.01); *A61M 2016/0036* (2013.01); *A61M 2016/102* (2013.01); *A61M 2230/43* (2013.01); *F04C 2270/041* (2013.01)

(58) Field of Classification Search
  CPC .. A61M 2230/43; A61M 16/14; A61M 16/16; A61M 2016/0021; A61M 2016/0027; A61M 2016/0036; A61M 2016/102
  See application file for complete search history.

(56) References Cited

U.S. PATENT DOCUMENTS

| | | | | |
|---|---|---|---|---|
| 6,534,769 B1* | 3/2003 | Graham | ................. | A61B 5/097 250/343 |
| 7,779,078 B2 | 8/2010 | Bang | | |
| 2003/0070681 A1* | 4/2003 | Rydgren | ................. | 128/204.18 |
| 2003/0196660 A1* | 10/2003 | Haveri | ............. | A61M 15/0085 128/203.12 |
| 2005/0056283 A1* | 3/2005 | Levi et al. | ................. | 128/204.21 |
| 2005/0284469 A1* | 12/2005 | Tobia | ................... | A61M 16/14 128/200.14 |
| 2006/0086254 A1 | 8/2006 | Bang | | |
| 2008/0091116 A1 | 4/2008 | Cardell et al. | | |
| 2008/0119754 A1* | 5/2008 | Hietala | ................. | A61B 5/087 600/532 |
| 2010/0065053 A1* | 3/2010 | Haveri | ............. | A61M 16/0833 128/204.18 |
| 2011/0000488 A1 | 1/2011 | Blomberg | | |
| 2011/0170852 A1 | 7/2011 | Numnual et al. | | |
| 2011/0265793 A1 | 11/2011 | Haveri | | |

OTHER PUBLICATIONS

Unofficial English Translation of Chinese Office Action and Search Report issued in connection with corresponding CN Application No. 201310051409.1 dated Nov. 4, 2015.

Unofficial English translation of Office Action issued in connection with corresponding CN Application No. 201310051409.1 dated Jul. 19, 2016.

Office Action issued in connection with corresponding EP Application No. 12155867.0, dated Jan. 27, 2017, 5 pages.

* cited by examiner

APPARATUS, ARRANGEMENT AND METHOD FOR ANALYZING BREATHING GAS FLOWING ALONG BREATHING TUBING FOR SUBJECT BREATHING

BACKGROUND OF THE INVENTION

This disclosure relates generally to an apparatus and method for analyzing a breathing gas flowing along a breathing tubing for subject breathing. Liquid particles are delivered intermittently depending on a phase of the breathing cycle or continuously into the breathing gas. Also this disclosure relates to a corresponding arrangement.

A tidal volume (TV) is an amount of an air inspired or taken into lungs in a single breath. TV is dependent on the sex, size, height, age and health, et cetera, of a patient, but in general TV also decreases as the size of the patient decreases. In an average healthy adult, TV is about 400-600 ml whereas in an average healthy neonate, that measures 3.5-4 kg and is 50 cm tall, TV is approximately 25-50 ml. On the other hand, in an average premature neonate that measures only 500 grams TV is only about 2-3.5 ml. TV of a smaller patient is very difficult to measure, but it can be approximated to 4-7 ml/kg, applying a general rule of thumb for approximating the TV of the human lung. In practice, the TV of a patient suffering pulmonary system deficiency is normally much less than the approximation gives.

A respiration rate (RR) is dependent on the sex, size, height, age and health, et cetera, of the patient, but in general RR increases as the size of the patient decreases. In an average healthy adult, RR is about 10-20 breaths/minute, whereas RR of a neonate may exceed as high as 150 breaths/minute.

When the patient is mechanically ventilated with a conventional ventilator, an endotracheal tube is placed into a trachea so that it goes through the oral or nasal cavity and larynx. The other end of the endotracheal tube is connected to a breathing circuit Y-piece through a luer type connector. If the patient is gas monitored with a mainstream or sidestream gas analyzer, an airway adapter, used for sampling the breathing gas that is analyzed by the gas analyzer, is normally connected between the endotracheal tube and the breathing circuit Y-piece connectors. During an inspiration, the fresh breathing gas, including higher oxygen ($O_2$) concentration, flows into the patient's lungs through an inspiratory limb of the breathing circuit Y-piece, the airway adapter, the endotracheal tube and their connectors, then to a trachea, a bronchus, a bronchi, bronchioles and finally reaching an alveoli deep in the lungs, where all the gas exchange actually occurs. Carbon dioxide ($CO_2$) molecules in a hemoglobin of a blood flowing in tiny blood vessels around the alveoli are replaced with $O_2$ molecules in the fresh breathing gas through the thin walls of the alveoli. $O_2$ molecules take their place in the hemoglobin, whereas $CO_2$ molecules flow out from the patient within the expired breathing gas, through the same path as the fresh gas came in during the inspiration. Thus a gas concentration of the breathing gas measured by the gas analyzer is somewhat proportional to the gas concentration in the blood.

A volume in a space between an intersection of the inspiratory and expiratory limbs of the Y-piece and the patient's mouth or nose, which is the beginning of oral and nasal cavities, is called a mechanical dead volume or dead space. A volume in a space between the patient's mouth or nose and the entrance of the alveoli is called an anatomical dead volume. The part of the lung that is injured or damaged for some reason and does not participate in the gas exchange is called a physical dead volume. As the used breathing gas flows out from the patient's lungs through the expiratory limb during expiration, a part of the used gas exits a pulmonary system, as well as the patient side of the breathing circuit, but remains in the mechanical and anatomical dead volume. Then as the fresh gas is inspired into the lungs through the inspiratory limb, the used gas already in the anatomical and mechanical dead volume flows into the lungs before the fresh gas. The used gas fills up some or all of the alveoli depending on a ratio of the dead volume and TV, or at least mixes with the fresh gas. This decreases the concentration of $O_2$ as well as increases the concentration of $CO_2$ in the lungs, which in turn decreases the gas exchange in the alveoli. This means that the larger the dead space, the larger the volume of the used gas, which has low $O_2$ and high $CO_2$ concentrations. As the used gas flows back to the patient's lungs during the inspiration, the gas exchange in the alveoli decreases. In other words, if the total dead volume is larger than TV, or as large as TV, the patient would not get any fresh gas into the lungs. Instead, the patient respires the used gas back and forth in the dead volume. In practice, a diffusion of gases assists the gas exchange over small dead volumes, especially when there is some movement of gases, such as high frequency ventilation evolves. However, the overall gas exchange in the alveoli would be lethal or dangerously poor.

The anatomical dead volume is very difficult to reduce, but it is proportional to the size and the physical condition of the patient. The mechanical dead volume depends on a breathing circuit design, an inner diameter of breathing circuit tubing, connectors and additional accessories, such as airway adapters used with a sidestream and mainstream gas analyzers. It is optimal that the mechanical dead space is zero as with normal breathing. The mechanical dead volume is more critical for smaller patients with smaller TV or patients suffering conditions such as, barotraumas, which decrease TV.

The mainstream gas analyzing is suitable for intubated patients or patients wearing a face or nasal mask. Mainstream analyzers are placed between the breathing circuit Y-piece and endotracheal tube, which is through their airway accessory used for measuring the gas concentration of the gas flowing through the analyzer. However, existing mainstream gas analyzers are big and heavy, and thus, very impractical to use. This is especially an issue with small patients, as the analyzer covers the patient's face and the analyzer's tiny endotracheal tube easily bends and clocks under the weight. Furthermore, accessories and additional connectors considerably add to the dead space, which is critical for a small patient with small TV. Also, the design of airway adapters and their non-tubular gas sampling chambers and connectors are inefficient. They generate turbulences in the breathing gas by mixing end tidal gas with fresh gas columns, thus mixing the gas samples that the mainstream analyzer tries to analyze, causing measurement inaccuracy, especially with higher RR and small TV. Currently, existing mainstream analyzers are not used with smaller patients.

The sidestream gas analyzers can be used with intubated and non-intubated patients. Sidestream analyzers are usually big and heavy and comprise complicated gas analyzing technology. As a result, they are placed further away from a patient and placed inside a host device, such as a patient monitor or ventilator. Gas samples are actively drawn into the analyzer with a gas pump through a sampling tube. When measuring intubated patients, the sampling tube is connected to a port in an airway adapter, which is placed between the breathing circuit Y-piece and an endotracheal tube. Gas samples are then drawn through the port, which is fluidly connected to the breathing gas flowing through the airway adapter. When measuring non-intubated patients, the sampling tube can be connected to nasal prongs, masks or straight into the nasal cavity to take gas samples from the gas flowing through the patient's upper airways.

The distance between the patient and the analyzer is usually very long, normally between 2-6 meters, which means gas samples travel a long distance before entering the analyzer. Gas samples drawn from the patient's breathing gas flow through the port in the airway adapter, through a connector between the sampling tube and the port, then through a 2-6 m long tiny tubing (inner diameter is usually between 0.8-1.5 mm), then through filters that separate water, mucus, and blood et cetera, and finally through membrane tubing. The membrane tubing has ionic properties that transfer water molecules through the membrane to even the humidity between the sample gas and the ambience. It is also possible to place filters between the port in the airway adapter and the sampling tubing followed by the membrane tubing to prevent liquids from entering the sampling tubing.

As gas samples travel through connectors, sample tubing and filters, the gas samples mix and average along the long path and therefore, comprise different concentrations. This considerably degrades the gas concentration measurement accuracy. Furthermore, the measurement accuracy degrades rapidly, especially when RR increases and TV decreases. This can be seen as damped and rounded capnogram, which is due to an increased number of smaller samples, or shortened gas columns that mix and average. This causes the amplitude of measured gas to decrease rapidly. The flow rate of sample gas has an effect on gas sample averaging. The lower the sample gas flow, the longer the gas columns travel through the tubing, et cetera, and the more they mix and average. Sample gas flow rates of existing sidestream gas analyzers are usually between 50-400 ml/min. As the flow rate of the sample gas is decreased, for example from 200 ml/min to 50 ml/min, the sensitivity to breathing gas concentration changes and decreases as the sample gas travels longer inside the tubing, et cetera, and mixes and averages more. It is possible to increase the flow rate of sample gas through the tube by decreasing the inner diameter of the tube. However, the negative pressure enabling the sample gas flow must be increased to keep the flow speed equal, which requires a more powerful pump. Gas columns may average even more as the flow speed of gas at the inner surface of the tube is zero and maximum in the middle of the tube. Smaller diameter tubing also tends to clog easier. For these reasons, most of the sidestream gas analyzer manufacturers specify the measurement range for RR only, which may go up to frequencies of 120-150 breaths/minute. However, the accuracy of the gas concentration measurement is not specified, or if it is specified, it only goes up to 15-60 breaths/minute, which is usable only for adults.

A nebulizer is a device used to deliver liquid form drugs into the patient's lungs in the form of a mist of small droplets called aerosol. Existing nebulizers are usually very big, clumsy, position sensitive and continuously produce the aerosol. Nebulizers are commonly placed between the inspiratory line, between the inspiratory limb of the breathing circuit Y-piece and the ventilator. Sometimes nebulizers are connected between the endotracheal tube and a manual resuscitator, especially when smaller patients are treated. However, this requires the patient to be naturally disconnected from the mechanical ventilator and ventilated manually. The aim is to produce the aerosol into the flowing inspiratory air to enable the aerosolized drug to enter the patient's lungs. However, as the existing nebulizers produce the aerosol continuously, during both inspiration and expiration and as the inspiration to expiration ratio of ventilation may be 1:1 or preferably 1:2, only a small part of the drug flows towards the patient's lungs.

When the nebulizer is connected between the inspiratory line, almost the whole line is continuously filled with aerosol continuously. During inspiration, only the gas column in the inspiratory line close to the Y-piece, which volume is proportional to patient's TV, flows towards the patient filling up the mechanical dead volume. When expiration starts, the aerosol in the dead volume flows towards the ventilator, but as the nebulizer produces the aerosol continuously, the aerosol produced during expiration flows straight out from the inspiratory line through the Y-piece and into the expiratory line. If existing nebulizers are placed between the breathing circuit Y-piece and the endotracheal tube, part of the aerosol produced during inspiration flows towards the patient, but aerosol generated during the expiration flows within the expired air away from the patient and into the ventilator and other devices connected to breathing circuit. Another problem with continuous aerosol production is similar to over humidification, where droplets produced into the motionless air come into contact with each other and combine into larger droplets. The droplets also come into contact with the breathing circuit walls, where they turn into liquid. Liquid then floats back and forth in the breathing circuit with the flowing air and may enter the patient's airways, which causes temporary airway obstruction, or even drowning. Liquid may also enter sensitive devices and analyzers connected to the breathing circuit, which causes malfunction, or even breakdown. There have been attempts for a nebulizer that can be turned on and off in regard to ventilation to increase the delivery efficiency, but such functioning devices do not currently exist on the market.

The functioning of other devices, such as sidestream gas analyzers that are connected between the breathing circuit Y-piece and the endotracheal tube, suffer from the aerosol or liquefied aerosol flowing back and forth within the flowing air. The optimum mean droplet diameter to ensure aerosol delivery into the deep lung and alveoli is between 1 and 5 microns. Thus, this size droplet easily enters the smallest cavities of devices connected to the breathing circuit. Aerosol flowing through the airway adapter disturbs the sidestream gas analyzers, especially during inspiration because they continuously draw gas samples and aerosol within the gas sample from the breathing circuit to generate a continuous real time capnogram of inspiratory and expiratory gases. Aerosol particles and liquefied aerosol easily flow into the sampling tubing, clogging the sampling tube and may even enter the filters and membrane tube, which may clog them as well. Many aerosolized drugs may include alcohol or other chemicals that may disturb and even destroy the functioning of filters and membranes when the aerosol or liquid may enter the very sensitive analyzing components, thus destroying the whole analyzer.

As a result, the existing sidestream gas analyzers are not very functional with existing nebulizers, as described earlier. Gas analyzing needs to be stopped and/or removed from the breathing circuit for the time of nebulization to prevent device malfunction. Gas analyzing also generates false measurement values during the nebulization that would further lead to incorrect estimation of a patient's condition and care practice.

BRIEF DESCRIPTION OF THE INVENTION

The above-mentioned shortcomings, disadvantages and problems are addressed herein which will be understood by reading and understanding the following specification.

In an embodiment, an apparatus is provided for analyzing a breathing gas flowing along a breathing tubing for subject breathing, the breathing gas comprising breathing cycles having different phases, liquid particles being delivered intermittently or continuously into the breathing gas depending on the phase of the breathing cycle. The apparatus comprises a gas sample supplier configured to adjust a gas sample supply from the breathing gas, a gas analyzer configured to receive the gas sample adjusted by the gas sample supplier and to measure the gas sample property of the breathing gas, and a processing unit configured to receive a signal indicative of one of the phases of the breathing cycle and the delivery timing of the liquid particles. The processing unit is further configured to control the gas sample supplier based on the signal received by the processing unit to limit access of liquid particles with the gas sample towards the gas analyzer.

In another embodiment, an arrangement is provided for analyzing a breathing gas flowing along a breathing tubing for subject breathing, the breathing gas comprising breathing cycles having different phases. The arrangement comprises an airway adapter operationally connectable to the breathing tubing for conveying the breathing gas. The airway adapter comprises a sample output connector for gas samples configured to be supplied along a sampling tube from the breathing gas during at least one of the phases of the breathing cycle. The arrangement further comprises a liquid supplier configured to deliver one of a liquid substance continuously and liquid particles intermittently into the breathing gas, and a gas sample supplier configured to adjust gas sample supply along the sampling tube from the breathing gas. Additionally, the arrangement comprises a gas analyzer configured to receive the gas sample adjusted by the gas sample supplier and to measure the gas sample property of the breathing gas, an indicator configured to provide a signal indicative of one of the phases of the breathing cycle and the delivery timing of the liquid supplier, and a processing unit configured to receive the signal from the indicator and to control the gas sample supplier based on the signal received to limit access of liquid particles with the gas sample towards the gas analyzer.

In yet another embodiment, a method is provided for analyzing a breathing gas flowing along a breathing tubing, the breathing gas comprising breathing cycles having different phases, liquid particles being delivered one of intermittently and continuously, depending on the phase of the breathing cycle, into the breathing gas for subject breathing. The method comprises adjusting a gas sample supply from the breathing gas and receiving the gas sample after adjusting for measuring the gas sample property of the breathing gas. The method also comprises receiving a signal indicative of one of the phases of the breathing cycle and the delivery timing of liquid particles, and controlling the adjustment of the gas sample supply based on the received signal to limit access of liquid particles with the gas sample supplied for measuring the gas sample property.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making reference to accompanying drawings. These detailed embodiments can naturally be modified and should not limit the scope of the invention as set forth in the claims.

Figure 1:
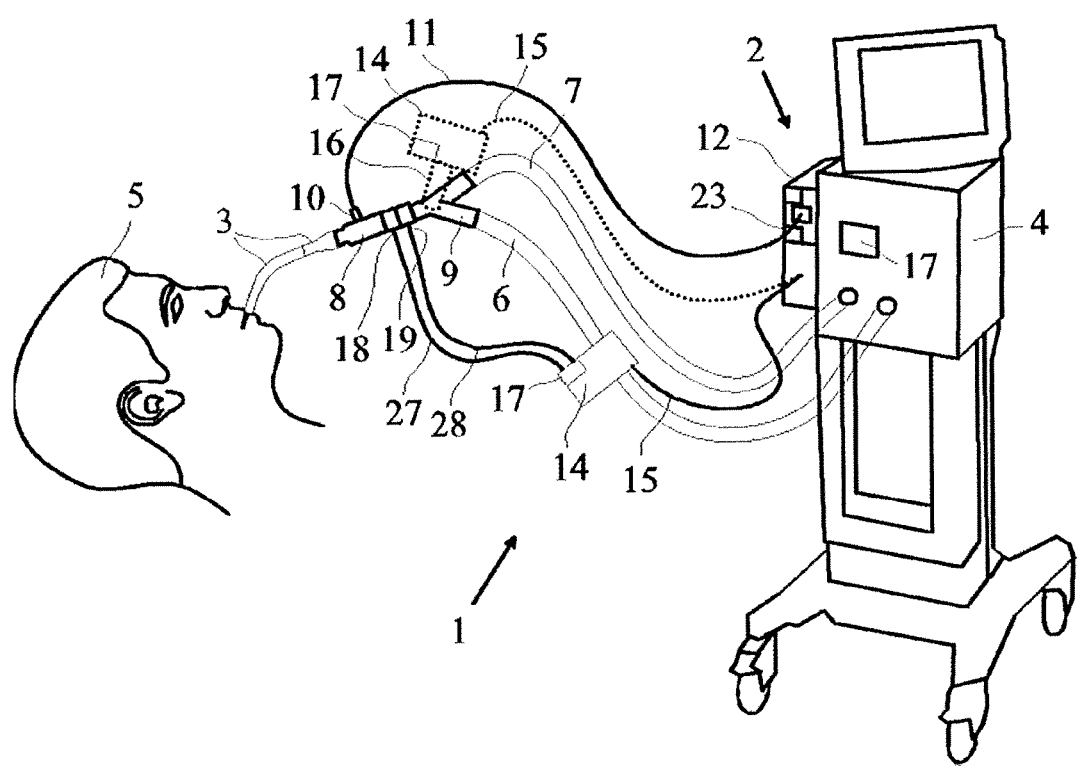
FIG. 1 is a schematic view of an arrangement of the apparatus in accordance with an embodiment of the present invention.

To enable gas analyzing during liquid supply, such as for nebulization or humidification, the resulting effects of liquid particles, such as aerosolized liquids, to gas analyzing need to be minimized or eliminated. FIG. 1 shows a schematic view of an arrangement 1 and an apparatus 2, for analyzing a breathing gas flowing along a breathing tubing 3, such as an endotracheal tube, wherein liquid particles can be delivered intermittently depending on a phase of a breathing cycle or continuously into the breathing gas for the subject breathing. Components of the apparatus may be part of the arrangement or separate from it. The phases of the breathing cycle are inhalation, exhalation and a time period between these two cycles that are transitions from one to another.

In an embodiment, the arrangement comprises a ventilator 4 connected to the subject 5 for assisting a breathing function of the subject 5. The ventilator 4 supplies along a first tubing 6, the volume of the breathing gas for an inspiration and receives along a second tubing 7, the volume of the breathing gas for an exhalation. This embodiment also comprises an airway adapter 8, such as a conventional sidestream type airway adapter, operationally connectable to the breathing tubing 3 for conveying the breathing gas. The airway adapter 8 is in flow connection with the first tubing 6, the second tubing 7, and the ventilator 4. The airway adapter 8 is typically between the ventilator 4 and the breathing tubing 3, which guides both the breathing gas for the exhalation from the lungs of a subject and the breathing gas for the inhalation to the lungs of the subject. The airway adapter 8 is provided with a sample output connector 10 for gas samples supplied along a sampling tube 11 from the breathing gas during at least one of the phases of the breathing cycle, typically during at least one of two phases, which are inspiration and expiration.

As shown in FIG. 1, between the airway adapter 8 and the ventilator 4 there is also a branching unit 9 having at least three limbs, one of said limbs being connected to the first tubing 6, another one being connected to the second tubing 7, and the third one being connected to the airway adapter 8. Additional limbs may be used to connect additional devices to enter the breathing circuit and/or the subject's lungs. A sampling tube 11 is connected to the sample output connector 10, which guides gas samples to a gas analyzer 12, such as a sidestream type gas analyzer. The gas analyzer 12 is part of the apparatus 2, and is placed outside the ventilator 4, but could as well be inside the ventilator.

An embodiment in FIG. 1 also comprises a liquid supplier 14, such as a nebulizer or a humidifier, for continuously delivering liquid substance into the breathing gas, or intermittently delivering liquid particles, such as liquid from drugs or water particles. In an embodiment, the liquid supplier 14 is connectable into the first tubing 6 between the branching unit 9 and the ventilator 4 to generate the liquid particles. For example, aerosol can be continuously delivered into the subject via the first tubing 6 within the inspiratory gas flow. The generation of liquid particles, including the drug, may also be intermittent in which case the liquid supplier 14 is turned on and off when needed. For example, the liquid supplier 14 can be turned on only for the time of inspiration and then turned off for the expiration. The liquid particles can also be generated only during the period between the inspiration and expiration, or in addition to the inspiration or expiration phases. As a result, the liquid supplier may function intermittently or continuously. Thus, the liquid particles can be generated into the first tubing 6 during inspiration and the generation of liquid particles can be turned off during expiration. This increases the delivery efficiency and minimizes the amount of wasted drug.

In an embodiment, the liquid supplier 14, which is a humidifier for water vapor delivery, is assembled between the breathing tubing 3 and the airway adapter 8. The active humidifier evaporates water particles from a separate liquid chamber into the breathing gas, in which case the humidifier can be connectable to any tubing between the ventilator 4 and the subject. As shown in the embodiment depicted in FIG. 1, the liquid supplier 14 is connected to the branching unit 9. Also, the humidifier could be placed between the airway adapter 8 and the branching unit 9. The production of liquid particle can be arranged similarly as described hereinbefore.

In an embodiment, the arrangement further comprises an indicator 17 for producing a signal indicative of the breathing cycle or the delivery timing of the liquid supplier. The indicator 17 provides a signal through a signal path 15 or the signal can be provided wirelessly. The indicator 17 can produce the signal regarding the breathing cycle based on the ventilator information in which case it may also be located in the ventilator. The indicator 17 can also produce a signal by way of a flow sensor 18 or a pressure sensor 19, in which case the indicator 17 may be located between the branching unit 9 and the breathing tubing 3. This allows the indicator 17 to indicate the direction of the gas flow, which may define or indicate an inspiration, an expiration, or a period between these two breathing phases. The indicator 17 may also be part of the liquid supplier 14 to provide information about the delivery timing of liquid particles into the breathing gas.

Figure 2:
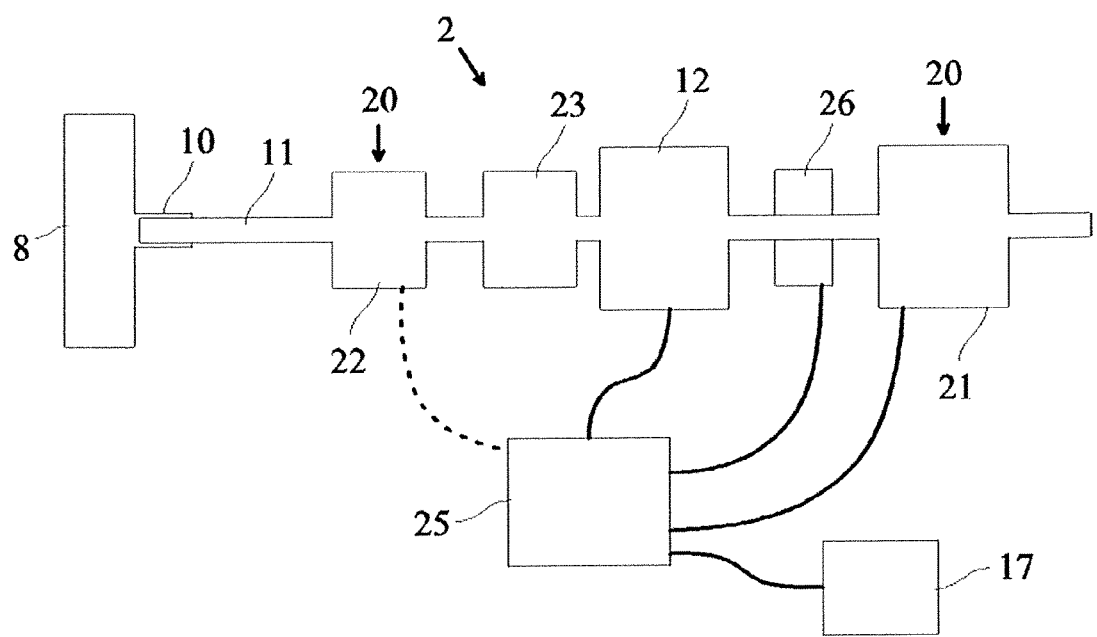
FIG. 2 is a detailed schematic view of an arrangement of the apparatus depicted in FIG. 1.

In the embodiment shown in FIG. 2, the apparatus comprising the gas analyzer 12 also comprises a gas sample supplier 20, such as a pump 21, or a combination of a valve 22 and a pump 21, which enables one to adjust the gas sample supply from the airway adapter 8 along the sampling tube 11 to the gas analyzer 12. In one embodiment, where the gas sample supplier 20 is a pump 21, the pump 21 is located downstream from the gas analyzer 12 to withdraw the gas sample through the analyzer to the pump. If the valve 22 and the pump 21 is used as the gas sample supplier, the valve 22 is located upstream of the pump 21. As shown in FIG. 2, the valve 22 is located upstream from the gas analyzer 12.

As shown in FIGS. 1 and 2, the apparatus in an embodiment may also comprise a liquid separator 23. This liquid separator 23 is located upstream of the gas analyzer to separate the liquid component following the gas sample withdrawn from the breathing gas flowing through the airway adapter 8. Thus, the liquid separator 23 separates the liquid component from the gas component. However, the liquid separator alone does not solve the problem discussed infra because there are liquids or liquid components which penetrate the liquid separator and cause harm to the gas analyzer.

As shown in the embodiment depicted in FIG. 2, a processing unit 25 is part of the apparatus to automatically control the gas sample supplier 20. The processing unit 25 can be separate or common with the gas analyzer receiving the signal indicative of gas sample properties, such as one of a respiration rate of a subject and a concentration of at least one component of the breathing gas from the gas analyzer 12. The processing unit 25 controls the sample gas supplier 20 based on the signal received from the indicator 17, which indicates the phase of the breathing cycle or the delivery timing of the liquid particles to limit access of liquid particles towards the gas analyzer 12. The gas sample supplier 20 is configured to decrease the sample flow rate without interrupting the sample flow in case it is advantageous to continuously supply at least a small amount of the sample gas. In such a case, the supplying rate is configured to decrease during an inspiration of approximately 40% to 70% compared to the mean supplying rate during the expiration. After the inspiration, where the sample gas supply was decreased or interrupted, the gas sample supplier is configured to increase sample flow rate or to restart the gas sample supply, if it was interrupted, from the breathing gas to supply a gas sample during an exhalation.

By decreasing the sample flow rate during the inspiration, liquid particles decrease in the flow to the sampling tube 11 and towards the gas analyzer 12. Thus, the negative effect of the liquid particles on the gas analysis is avoided. However, in most cases it might be advisable to pause the sample gas flow during the inspiration because the breathing gas flowing towards the subject includes liquid particles of higher concentration and maybe of higher volume than during the expiration. Also, samples of the breathing gas supplied during the expiration enable control of vital functions of the subject than those breathing gas samples acquired during the inspiration. But occasionally, the gas samples of the inspiration may also be needed to control the subject.

In an embodiment shown in FIG. 2, a sample flow sensor 26 upstream from the gas sample supplier 20, or the gas analyzer 12, is useful and may be included when the sample gas flow rate is measured. The signal indicative of the sample gas flow rate can be fed to the processing unit 25 to control the sample gas flow rate. The flow rate of supplied gas should not be too high that it harms the subject, as drawing too much breathing gas from the lungs can collapse the lungs. However, if the flow rate of supplied gas is too low, especially during expiration, the gas concentration or respiration rate values would not be accurate. If an accurate capnogram is desired, the flow rate of supplied gas should be measured accurately to restore the correct time line, especially when decreasing the sample flow rate without interrupting the sample flow. When the liquid supply is not present, the flow rate of supplied gas is kept constant to get a uniform capnogram.

In an embodiment, the signal that activates the generation or delivery of liquid particles is derived along the signal path 15 from the ventilator 4. This signal can be based on the ventilator working cycle or a ventilator flow or pressure. The signal can also be derived along signal path 27, which is from the flow sensor 18, and/or along a signal path 28, which is from the pressure sensor 19 connected to a breathing circuit that measures the flow, and/or via the pressure of breathing gas delivered into the subject during inspiration and removed from the patient during expiration. It is also possible that the liquid supplier 14 has a measuring device, such as a pressure sensor, to measure breathing gas pressure and/or a flow sensor to measure flow for turning on and off the liquid particle delivery, such as for nebulization.

As already explained hereinbefore, when the liquid particle delivery occurs, the gas sample supplier 20 may be paused, such as turned off for the time of inspiration to prevent liquid particles, such as aerosol, from entering the gas analyzing system. The liquid particles enter the gas analyzing system by flowing within the inspiratory air that comes from the first tubing 6, through the airway adapter 8, passed the sample output connector 10, and then into the gas analyzer. This may also mean that the gas analyzing is paused because new samples are not received. In an embodiment, the liquid supplier 14, or the host device in which the liquid supplier and the gas analyzer 12 are connected to, such as the ventilator 4, automatically inform the processing unit 25 to turn the gas sample supplier 20 into a functional mode in which the gas analyzer's sample gas flow is paused or readjusted for the time of the liquid particle delivery. Pausing is based on the same signals as described previously for the liquid supplier 14, or the liquid supplier can provide the signal. It is also possible to switch a bypass valve from the gas analyzer 12 (not shown in FIG. 1) to draw zero gas into the gas analyzer, such as filtered room air, that can be used for zeroing the gas measurement.

During inspiration, the liquid particles flow within the inspiratory air through the airway adapter 8 and into the subject's lungs. However, as the gas sample flow is zero, the liquid particles do not flow through the sample output connector 10 and into the sampling tube 11. Therefore, the gas analyzer 12 keeps clean and dry of liquid particles. However, during expiration, the sample gas flow is turned on to enable the gas to flow from the breathing circuit, through the sample output connector 10 into the sampling tube 11, and into the gas analyzer 12, where it is analyzed. Whether the liquid supplier 14 produces the liquid particles continuously or if it is turned off for the time of expiration, the liquid particles coming from the first tubing 6 will flow away from the subject towards the second tubing 7 and ventilator 4. Thus, the access of liquid particles into the gas analyzer 12 is substantially prevented. To ensure that the liquid particles in aerosol do not flow into the gas analyzer 12, the liquid supplier can be turned off for the time of expiration.

Normally, when liquid particle delivery is not present, the gas analyzer would show a continuous capnogram, including inspiratory and expiratory values, but when the liquid particle delivery is present, it shows the end tidal (ET) values of breathing gas. However, a continuous capnogram is important information to understand in the gas exchange in order to control proper ventilation of the subject's lungs.

In an embodiment, the liquid supplier 14 is connected between the branching unit 9 and the airway adapter 8. This embodiment also prevents liquid particles from entering the gas analyzer 12 by pausing or adjusting the sample gas flow for the time of inspiration. During expiration, whether the liquid particle delivery is continuous or intermittently synchronized to inspiration, the expiratory air flowing out from the patient flushes the liquid particles in the breathing air towards the second tubing 7. Thus, preventing the aerosol from entering into the gas analyzer 12.

If the liquid supplier 14 is connected between the airway adapter 8 and the breathing tubing 3, the liquid supplier 14, which continuously generates the liquid particles, could not be used, especially if gas analyzing is desired. During inspiration, the liquid particles would naturally flow straight into the subject's lungs, but during expiration, the liquid particles would flow towards the second tubing 7, through the airway adapter 8, and into the gas analyzer 12 as the gas sample supplier draws gas samples to get ET values for the expiratory gases coming from the patient. A liquid supplier that can be synchronized to inspiration would work well, but in either case, as well as that explained hereinbefore, when the liquid supplier is placed between the branching unit 9 and the breathing tubing 3, the dead volume that a nebulizer adds into the breathing circuit would be high; thus, causing rebreathing of gases. Further, such a liquid supplier could not be used with smaller subjects.

The embodiments depicted in FIG. 1 also show an alternative place for the liquid supplier 14, where it is connected into a fourth port 16 of branching unit 9, provided that such port exists in the branching unit. The liquid supplier 14 is positioned close to the intersection of the first tubing 6 and the second tubing 7 so that liquid particle delivery is as close to the subject as possible. Since the fourth port 16 is not in the path common for inspiratory and expiratory gases, and as there is no air flow through the fourth port, the liquid supplier or the port 16 do not add dead volume into the breathing circuit.

If the liquid supplier 14 continuously generates the liquid particles during inspiration, the liquid particles flow from the port 16 into the subject 5 within the inspiratory air. During expiration, the liquid particles flow away from the subject 5, straight from the first tubing 6, into the second tubing 7, and towards the ventilator 4. Samples of breathing gases can be analyzed by pausing the sample gas flow for the time of inspiration and starting the sample gas flow again for the time of exhalation. Even to minimize the flow of liquid particles into the gas analyzer the sample gas flow can be turned on after a predetermined time delay in regard to the start of exhalation. The length of the time delay is typically short, but proportional to the time that is needed to empty the dead volume of breathing gas including liquid particles before the used gas coming from the patient's lungs flushes the dead volume of air with liquid particles.

If the liquid supplier 14 is turned on to generate liquid particles for the time of inspiration and turned off to stop liquid particles generation for the time of expiration, the delivery efficiency of liquid particles is increased as more liquid particles flow into the patient's lungs and less liquid particles are wasted into the breathing circuit and connected devices. Breathing gases are analyzed by pausing the sample gas flow for the time of inspiration and restarting the sample gas flow again for the time of expiration. To minimize the flow of liquid particles into the gas analyzer, the sample gas flow is turned on after a predetermined time delay in regard to the start of exhalation. The length of time delay is typically short, but proportional to the time that is needed to empty the dead volume of air comprising liquid particles before the used gas coming from the patient's lungs flushes the dead volume of air with liquid particles. Another way to minimize the flow of liquid particles into the gas analyzer is to stop the delivery of liquid particles shortly before the end of inspiration. This minimizes the delivery of liquid particles into the dead volume of the breathing circuit. When the exhalation starts, the dead volume is already empty of liquid particles and the sample gas flow is turned on just at the beginning of exhalation.

If inspired gases need to be analyzed during the delivery of liquid particles and if the liquid supplier is available, liquid particle generation can be turned on and off freely, which makes it possible to stop or skip liquid particle delivery during every second, third, fourth, etc. inspirations. During these inspirations, when the liquid particle delivery is stopped, the gas sample supplier 10 can draw gas samples from the breathing circuit to be analyzed by the gas analyzer 12. As inspired gas measurement values are used less frequently than expired values, gas analyzing during some inspiration would increase the time of the liquid particle delivery depending on how frequently it is executed.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples or embodiments that occur to those skilled in the art. Such other examples or embodiments are intended to be within the scope of the claims if they have structural elements that do not differ from the literal language of the claims, or if they include equivalent structural elements with insubstantial differences from the literal languages of the claims.

The invention claimed is:

1. An apparatus for analyzing a breathing gas flowing along a breathing tubing for subject breathing, the apparatus comprising:
    a gas sample supplier fluidly connected to the breathing tubing and configured to draw gas samples from the breathing gas;
    a gas analyzer fluidly connected to the gas sample supplier and configured to receive the gas samples from the gas sample supplier and analyze the gas samples; and
    a processing unit configured to:
        receive a signal indicative of a current phase of the subject breathing in a breathing cycle;
        control the gas sample supplier to supply the gas samples to the gas analyzer at a first value of sample flow rate in response to the current phase being an inhalation;
        control the gas sample supplier to suppy the gas samples to the gas analyzer at a second value of sample flow rate in response to the current phase being an exhalation, wherein the second value of sample flow rate is greater than the first value of sample flow rate; and
    wherein the first value of sample flow is 40% to 70% less than the second value of sample flow rate.

2. The apparatus of claim 1, further comprising a liquid separator located upstream of the gas analyzer and configured to separate a liquid component from the gas samples, wherein the gas analyzer is configured to meaure a respiration rate of the subject breathing and a concentration of at least one component of the breathing gas.

3. The apparatus of claim 1, further comprising a sample flow sensor configured to measure the sample flow rate.

4. The apparatus of claim 1, wherein the breathing gas comprises liquid particles delivered intermittently or continuously by a liquid supplier, and the processing unit is further configured to:
    control the gas sample supplier to decrease the sample flow rate if a concentration or a volume of the liquid particles in the gas samples is increasing; and
    control the gas sample supplier to increase the sample flow rate if the concentration or the volume of the liquid particles in the gas samples is decreasing.

5. The apparatus of claim 1, wherein the gas sample supplier comprises a pump configured to withdraw the gas samples from the breathing gas.

6. The apparatus of claim 1, wherein the gas sample supplier comprises a valve and a pump, the valve is located upstream of one of the gas analyzer and the pump.

7. An arrangement for analyzing a breathing gas flowing along a breathing tubing for subject breathing, the arrangement comprising:
    an airway adapter connected to the breathing tubing, the airway adapter comprising a sample output connector configured to output gas samples from the breathing gas,
    a sampling tube connected to the sample output connector and configured to convey the gas samples,
    a gas sample supplier connected to the sampling tube and configured to draw the gas samples from the breathing gas;
    a gas analyzer fluidly connected to the gas sample supplier and configured to receive the gas samples from the gas sample supplier and analyze the gas samples;
    an indicator configured to provide a signal indicative of a current phase of the subject breathing in a breathing cycle; and
    a processing unit configured to:
        receive the signal indicative of the current phase;
        control the gas sample supplier to supply the gas samples to the gas analyzer at a first value of sample flow rate in response to the current phase being an inhalation; and
        control the gas sample supplier to suppy the gas samples to the gas analyzer at a second value of sample flow rate in response to the current phase being an exhalation, wherein the second value of sample flow rate is greater than the first value of sample flow rate; and
    wherein the first value of sample flow rate is 40% to 70% less than the second value of sample flow rate.

8. The arrangement of claim 7, further comprising a liquid supplier configured to deliver liquid particles to the breathing gas intermittently or continuously, wherein the processing unit is further configured to:
    control the gas sample supplier to decrease the sample flow rate if a concentration or a volume of the liquid particles in the gas samples is increasing; and
    control the gas sample supplier to increase the sample flow rate if the concentration or the volume of the liquid particles in the gas samples is decreasing.

9. The arrangement of claim 7, wherein the gas sample supplier comprises a pump configured to withdraw the gas samples from the breathing gas.

10. A method for analyzing a breathing gas flowing along a breathing tubing for a subject breathing, the method comprising:
    drawing gas samples from the breathing gas;
    determining a current phase of the subject breathing in a breathing cycle;
    supplying the gas samples to a gas analyzer at a first value of sample flow rate in response to the current phase being an inhalation;
    supplying the gas samples to the gas analyzer at a second value of sample flow rate in response to the current phase being an exhalation;
    wherein the second value of sample flow rate is greater than the first value of sample flow rate;
    wherein the first value of sample flow rate is 40% to 70% less than the second value of sample flow rate; and
    analyzing the gas samples.

11. The method of claim 10, wherein the current phase is determined based on a direction of gas flow of the breathing gas along the breathing tubing.

12. The method of claim 10, further comprising separating a liquid component from the gas samples.

13. The method of claim 10, wherein analyzing the gas samples comprises meauring a respiration rate of the subject breathing and a concentration of at least one component of the breathing gas.

14. The method of claim 10, further comprising:
    delivering liquid particles intermittently or continuously to the breathing gas;
    decreasing the sample flow rate if a concentration or a volume of the liquid particles in the gas samples is increasing; and
    increasing the sample flow rate if the concentration or the volume of the liquid particles in the gas samples is decreasing.

* * * * *